United States Patent [19]
Campbell, Jr.

[11] Patent Number: 5,261,908
[45] Date of Patent: Nov. 16, 1993

[54] EXPANDABLE VERTICAL PROSTHETIC RIB

[76] Inventor: Robert M. Campbell, Jr., 415 Stone Wood, San Antonio, Tex. 78216

[21] Appl. No.: 768,742

[22] PCT Filed: Apr. 14, 1990

[86] PCT No.: PCT/US90/02018
§ 371 Date: Oct. 21, 1991
§ 102(e) Date: Oct. 21, 1991

Related U.S. Application Data

[63] Continuation-in-part of Ser. No. 338,227, Apr. 14, 1989, Pat. No. 5,092,889.

[51] Int. Cl.[5] .................... A61B 17/56; A61F 2/44
[52] U.S. Cl. .................... 606/61; 623/17; 403/106; 403/109; 403/241
[58] Field of Search .................... 623/16, 17; 606/60, 606/61, 63, 64, 69, 70, 71, 74; 403/106, 108, 241, 109

[56] References Cited

U.S. PATENT DOCUMENTS

| | | | |
|---|---|---|---|
| 864,329 | 8/1907 | North | 403/108 |
| 1,049,398 | 1/1913 | Rice | 403/108 X |
| 2,484,401 | 10/1949 | Coie | 403/108 X |
| 2,662,420 | 12/1953 | French et al. | 403/108 X |
| 3,495,796 | 2/1970 | Fruh et al. | 403/108 X |
| 4,279,248 | 7/1981 | Gabbay | 606/151 X |
| 4,606,335 | 8/1986 | Wedeen | 606/74 X |
| 5,030,235 | 7/1991 | Campbell | 623/16 |
| 5,092,889 | 3/1992 | Campbell | 623/16 |

*Primary Examiner*—Randall L. Green
*Attorney, Agent, or Firm*—Gunn, Lee & Miller

[57] ABSTRACT

Applicant's invention includes a prosthetic rib (10) which is adjustable in length through relatively minor surgical procedures subsequent to initial implantation along with methods for using same in the treatment of chest wall deformities and scoliosis and in immobilizing fractured ribs. The prosthetic rib (10) is designed for secure attachment to existing natural ribs (12) in a manner which minimizes constricture thereof, provides substantial torsional stability, and permits the prosthesis to accommodate traumatic impact thereto while resisting fracture of the associated natural ribs (12).

6 Claims, 12 Drawing Sheets

FIG. 3a  FIG. 3c

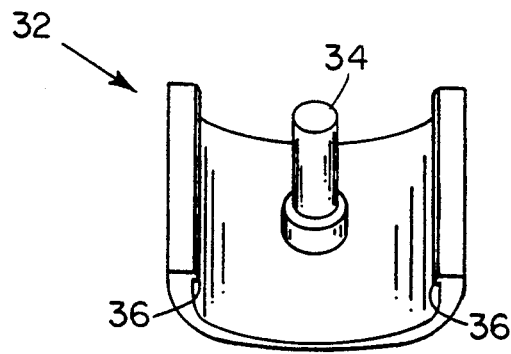
FIG. 5a
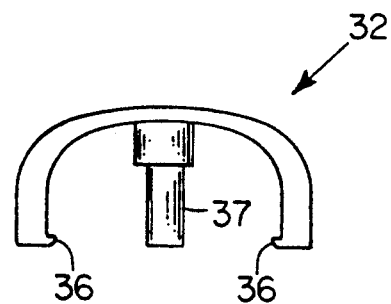
FIG. 5b
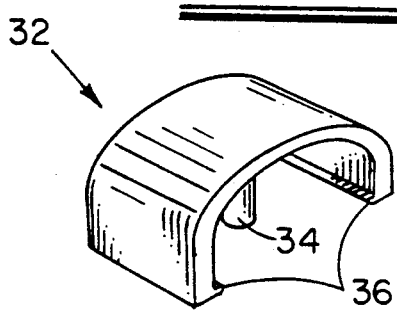
FIG. 5c
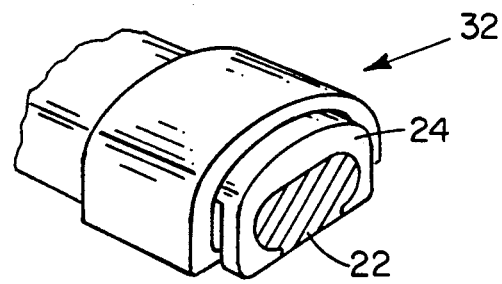
FIG. 5d
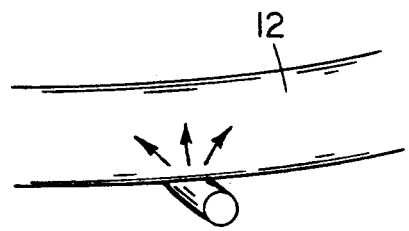
FIG. 6a
FIG. 6b

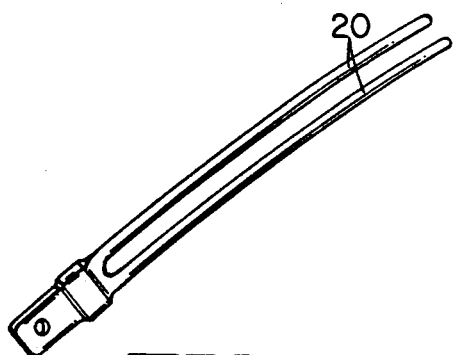
FIG. 7a
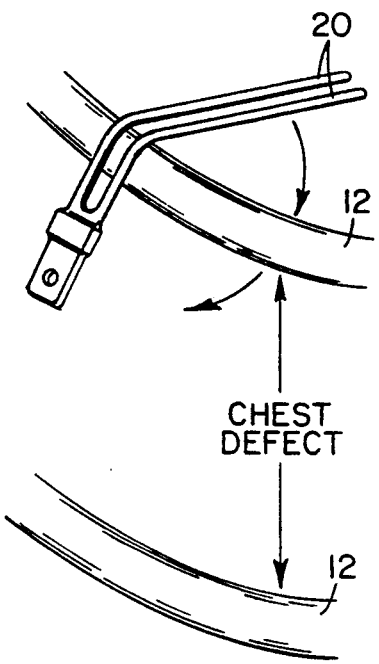
CHEST DEFECT
FIG. 7b
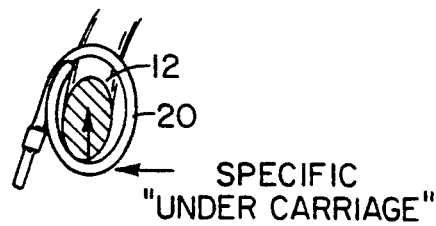
SPECIFIC "UNDER CARRIAGE"
FIG. 7c
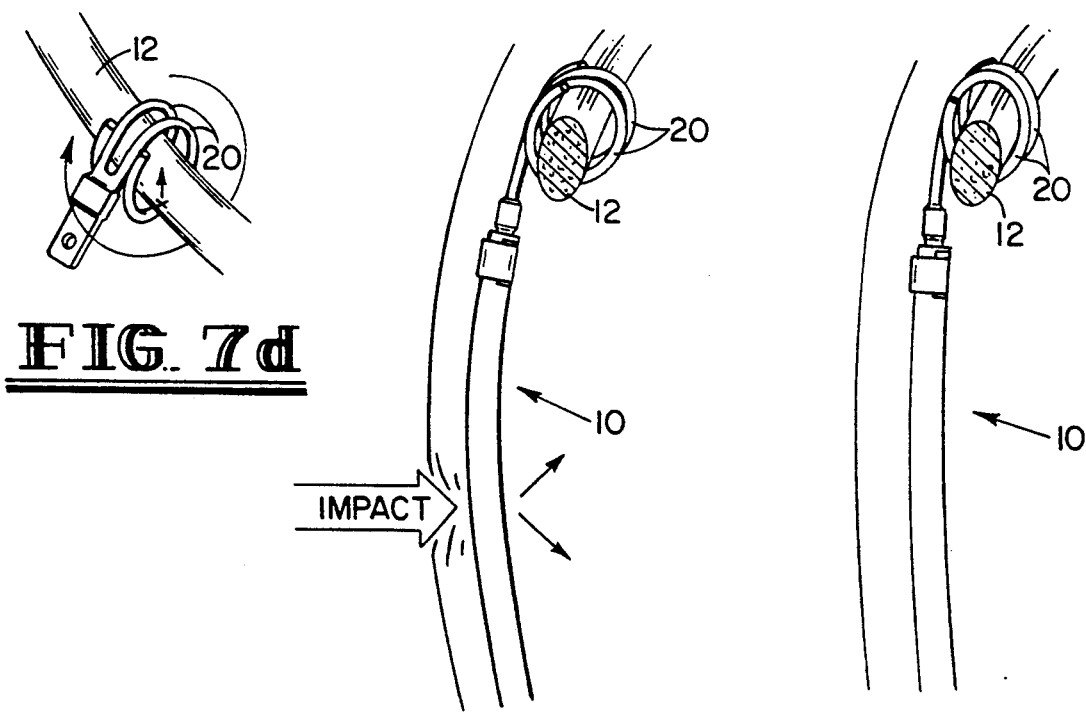
FIG. 7d
IMPACT
FIG. 8a    FIG. 8b

EXPANDABLE VERTICAL PROSTHETIC RIB

REFERENCE TO PRIOR U.S. APPLICATION

This is a continuation-in-part application with respect to U.S. patent application Ser. No. 07/388,227 filed Apr. 14, 1989, now U.S. Pat. No. 5,092,889.

FIELD OF THE INVENTION

Applicant's invention pertains to the field of prosthetic skeletal devices primarily for use in humans.

BACKGROUND OF THE INVENTION

Applicant's invention relates, in part, to the prosthetic replacement of ribs which are absent or effectively non-functional as a congenital condition or as a result of injury or disease. Applicant's invention further relates, in part, to a novel treatment of scoliosis and of symptoms commonly associated therewith. Finally, the device of Applicant's invention may be used as a platform to which fractured ribs may be attached during the healing process.

Presently, ribs which are actually or effectively absent due to trauma or congenital defect may be prosthetically replaced to a limited degree. The presently available and moderately effective prosthesis consists of one or more steel rods attached to and spanning vertically between existing natural ribs. This creates an artificial albeit perpendicularly oriented substitute for the missing ribs and vital protection for the cardiovascular and peripheral tissues.

The presently available prosthesis has significant limitations, the most notable of which when used in children is its inability to accommodate growth. As a child grows the distance between any two natural ribs increases. To prevent substantial disfigurement, possible injury to the spinal column, and constriction of the cardiovascular system, the radical surgical procedure of implanting the presently available prosthesis must be repeated periodically to implant longer prostheses.

Scoliosis is a condition evidenced by abnormal curvature of one or more segments of the vertebral column. Scoliosis in its extreme forms results in tragic disfigurement and injury to the spinal cord. A vertebral column affected by scoliosis often assumes a serpentine configuration when viewed posteriorly or anteriorly.

At present, generally accepted treatment for scoliosis is available in two forms: 1) forced reorientation through the use of external braces; and 2) posterior spinal fusion. Even with adult patients, braces slip, are uncomfortable and confining, and lack direct access to the skeletal components (the ribs) which they are intended to manipulate. In children, particularly the very young, braces constitute a completely impractical treatment option. Spinal fusion is likewise undesirable, particularly with respect to young children, because growth of the spinal column is permanently arrested. In the case of a very young child for whom spinal fusion is performed, his or her vertebral column will remain at its present size while the rest of the body grows at a more or less normal rate. The resulting disfigurement is profound and, in fact, life threatening in some cases.

Both rib humps and chest concavities may be modified in an aesthetically desireable manner by altering the rib structure which contributes to the deformity. Such alteration involves selectively fracturing, reorienting, and (in some cases) effecting a gradual elongation of the involved ribs. The fractured ribs in any case should be immobilized to promote fast healing with the intended final orientation.

Applicant's invention addresses each of the above-identified situations with respect to prosthetic rib replacement and the treatment of scoliosis and is further useful in the immobilization of fractured ribs, whether fractured through trauma or as part of treatment of rib deformities.

SUMMARY OF THE INVENTION

It is an object of the present invention to provide an improved prosthesis for the replacement of missing or damaged human ribs.

It is another object of the present invention to provide a novel prosthetic rib which accommodates growth of a recipient.

It is another object of the present invention to provide a novel prosthetic rib which is adjustable in length to accommodate patients with differing physiological dimensions.

It is another object of the present invention to provide a novel prosthetic rib which has means for secure attachment to existing ribs yet minimizes ischemia and accommodates benign movement and reorientation of the rib.

It is another object of the present invention to provide a prosthetic rib which accommodates traumatic impact in a manner which minimizes the risk of fracture of natural ribs to which the prosthesis is attached.

It is another object of the present invention to provide a prosthetic rib which provides an optimal balance between effective prosthesis and safety in implantation.

It is another object of the present invention to provide a prosthetic rib which may be indefinitely implanted in a child notwithstanding later growth of such child.

It is another object of the present invention to provide a novel device for use in the treatment of scoliosis exhibiting as yet unavailable benefits.

It is another object of the present invention to provide a novel device for use in the treatment of scoliosis which device obviates any need for using external braces.

It is another object of the present invention to provide a novel device for use in the treatment of scoliosis which device obviates any need for performing spinal fusion as a means for treatment.

It is another object of the present invention to provide a device for use in the treatment of scoliosis which device accommodates growth by the recipient.

It is another object of the present invention to provide a novel device for use in the treatment of scoliosis the length of which device may be adjusted through minor surgical procedures after initial implantation to meet contingencies arising after initial implantation which indicate such adjustment.

It is another object of the present invention to provide a novel device to which fractured ribs may be attached and immobilized to facilitate the healing process.

It is another object of the present invention to provide an improved method for the prosthetic replacement of missing ribs in humans.

It is another object of the present invention to provide an improved method for the treatment of scoliosis.

It is another object of the present invention to provide a novel, improved device for the immobilization of fractured ribs.

It is another object of the present invention to provide a novel and improved method for the treatment of rib humps and chest concavities and convexities involving the use of a novel, improved device for the immobilization of ribs fractured in the process.

In satisfaction of some of the stated objectives, Applicant's present invention provides a device and method for using such device associated therewith which device may serve as a prosthetic rib which is adjustable in length through relatively minor surgical procedures subsequent to initial implantation. Some embodiments of the device are designed for secure attachment to existing natural ribs in a manner which minimizes constricture thereof, provides substantial torsional stability, and permits the prosthesis to accommodate traumatic impact thereto while resisting fracture of the associated natural ribs.

In satisfaction of other stated objectives, Applicant's just-described device and an alternative method for use associated therewith serves to alter the relative orientation of ribs to which such device is attached and thereby modify the orientation of the associated vertebrae as well as the vertebrae therebetween in the treatment of scoliosis.

In satisfaction of still further stated objectives, the above-described device, with slight modifications, and yet another method for use associated therewith serves to immobilize ribs fractured by way of trauma, whether accidental or intentional in the treatment of rib deformities.

All embodiments of the device of Applicant's invention are adjustable in length through relatively minor, post-implantation surgical procedures.

BRIEF DESCRIPTION OF THE DRAWINGS

FIG. 3a is a top plan view of the rib sleeve of Applicant's invention.

FIG. 3c is a cross sectional view of the rib sleeve of Applicant's invention.

FIG. 5a is a perspective view of the inner surface of the distraction lock of Applicant's invention.

FIG. 5b is an elevational view of the inner surface of the distraction lock of Applicant's invention.

FIG. 5c is a perspective view of the outer surface of the distraction lock of Applicant's invention.

FIG. 5d is a perspective view of the distraction lock of Applicant's invention placed on a length of the rib sleeve.

FIG. 6a is a depiction of the rounded rod of Applicant's invention as it contacts the natural rib of a recipient.

FIG. 6b is a depiction of an angular rod, a taught against by Applicant's invention, as it would contact the natural rib of a recipient.

FIG. 7a is a partial perspective view of the rib sleeve carriage attachment of Applicant's invention.

FIG. 7b is a partial perspective view of the rib sleeve carriage attachment of Applicant's invention with the rods thereof bent as for initial implantation procedures.

FIG. 7c is a partial perspective view of Applicant's rib sleeve carriage attachment with the rods thereof encircling a natural rib of a recipient according to the teaching of Applicant's invention.

FIG. 7d is a cross sectional view of Applicant's rib sleeve carriage attachment with the rods thereof encircling a natural rib of a recipient according to the teaching of Applicant's invention.

FIGS. 8a and 8b are serial representation of the action of the Applicant's prosthetic rib in absorbing impact.

FIG. 14b is a representation of the tips of the pliers shown in FIG. 14a

FIG. 16b is a representation of the sheet of medical elastomeric plastic material of FIG. 16a.

Detailed Description of the Preferred Embodiment

A. Use of Applicant's Device as a Prosthetic Rib

Figure 1:
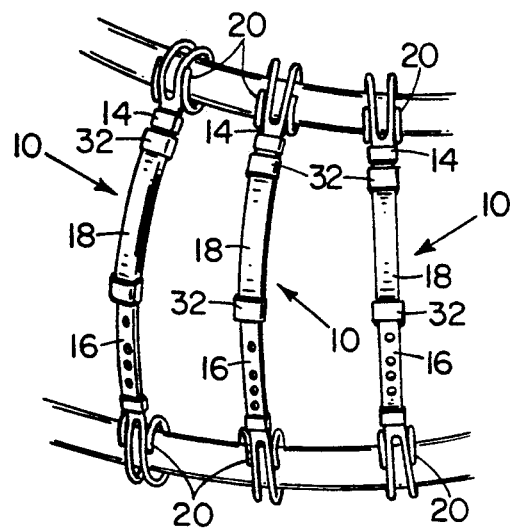
FIG. 1 is a perspective view a number of implanted device of applicant's design.

Referring to FIG. 1, a first embodiment of the device of Applicant's invention (hereinafter usually referred to as the "prosthetic rib") is identified generally by the reference numeral (10). As is apparent from FIG. 1, multiple prosthetic ribs (10) will typically be implanted to span between existing natural ribs (12) to compensate for an abnormal absence of intervening natural ribs (12).

The prosthetic rib (10) is designed to be adjusted in length subsequent to implantation. The primary purpose of the adjustability being to accommodate growth of a child in whom the prosthetic rib (10) is implanted. The adjustability is also a benefit in using a single sized prosthetic rib (10) for applications requiring varying rib lengths. This permits use of a single sized rib (10) in a single patient in different positions or in different patients with varying physiological dimensions. Both of these scenarios have obvious financial benefits to the patient(s) when compared with having a number of custom fabricated prostheses made for very specific, limited applications.

Figure 2A:
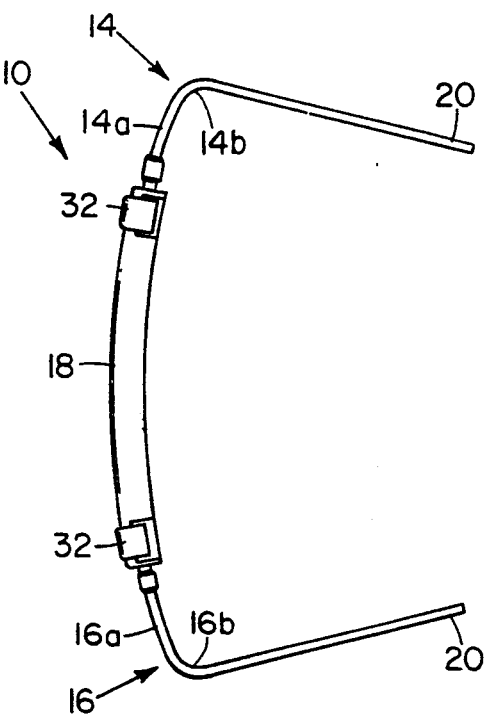
FIG. 2a is an elevational view of the device of Applicant's invention in a contracted configuration rib sleeve being shown as transparent.
Figure 2B:
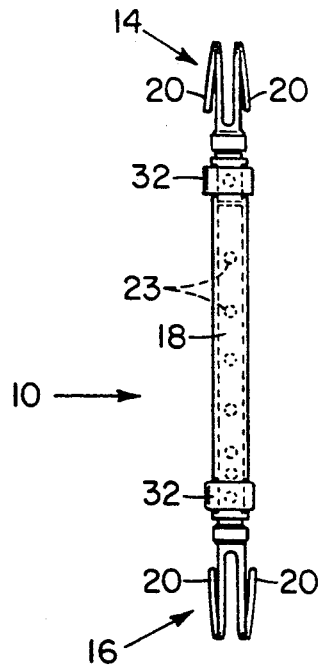
FIG. 2b is a top plan view of the device of Applicant's invention in a contracted configuration with the rib sleeve being shown as transparent.
Figure 2C:
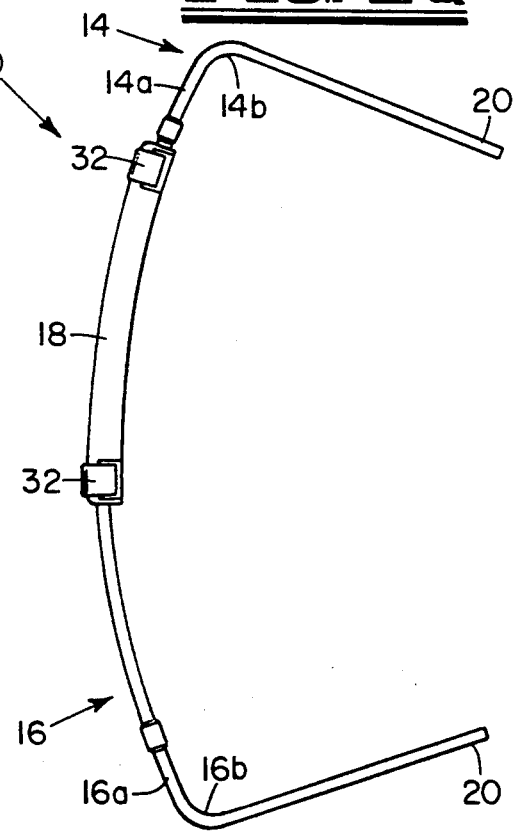
FIG. 2c is an elevational view of the device of Applicant's invention in an extended configuration.

Referring to FIGS. 2a, 2b, and 2c, the prosthetic rib (10) comprises three principal components: a rib sleeve carriage attachment (14), a rib shaft/rib shaft carriage attachment (16), and a rib sleeve (18). The rib shaft/rib shaft carriage attachment (16) is a single object of unitary construction, but for discussion purposes may be divided between the rib shaft (16a) and the rib shaft carriage attachment (16b). Unless otherwise specified, all components of the prosthetic rib (10), except the rib sleeve (18) which is made of Titanium Alloy 64, are manufactured of Commercially Pure (CP) Titanium. The use of titanium is dictated by the strength and flexibility requirements for the components of the prosthetic rib (10) in light of the dimensions of such components. Other materials, such as surgical grade stainless steel, may be used in constructing the prosthetic rib (10), but at the expense of the optimum balance of benefits derived from titanium. Another benefit arising from the use of titanium is derived from the fact that it is not a ferromagnetic metal. As such, titanium is compatible with magnetic resonance imaging (M.R.I.) scanning, a much preferable diagnostic procedure, particularly with patients who would normally be considered as recipients of Applicant's prosthetic rib 10.

The combined rib shaft (16a) and rib sleeve (18) serve as the actual prosthesis. The rods (20) of the carriage attachments (14) and (16b) serve as the attachment means for anchoring the prosthetic rib (10) to natural ribs (12) and will be discussed in detail hereinafter.

Figure 3B:
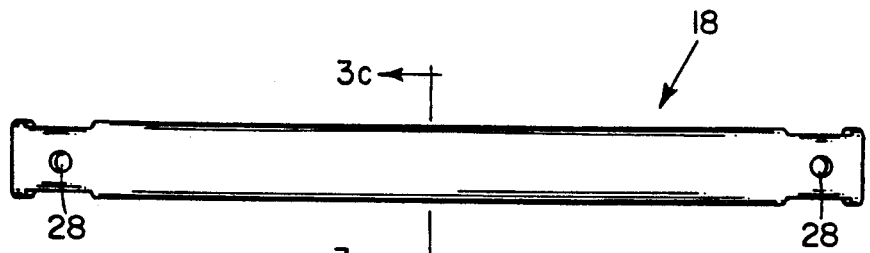
FIG. 3b is an elevational view of the rib sleeve of Applicant's invention.
Figure 3B:
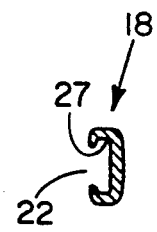
Figure 3B:

Referring again to FIGS. 2a, 2b, and 2c, and also to FIGS. 3a, 3b, and 3c, the rib sleeve (18) may be described as an open, semi-oval with a lengthwise oriented channel (22) interrupting the lower surface of the rib sleeve (18). The presence of the channel (22) is in response to manufacturing cost limitations. It should be understood that a suitable alternative sleeve which lacks the channel (22) entirely (not shown in the drawings) would be acceptable for the purposes stated herein, but would be available, if at all, at a considerably higher price because of difficulties in manufacturing such a sleeve. For that reason, the depicted rib sleeve (18) would be considered a preferred embodiment.

Figure 4A:
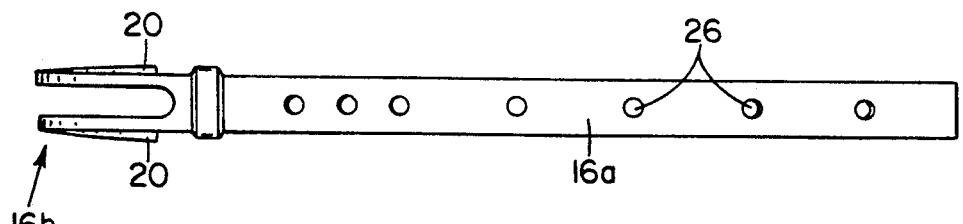
FIG. 4a is a top plan view of the rib shaft/rib shaft carriage attachment of Applicant's invention.
Figure 4B:
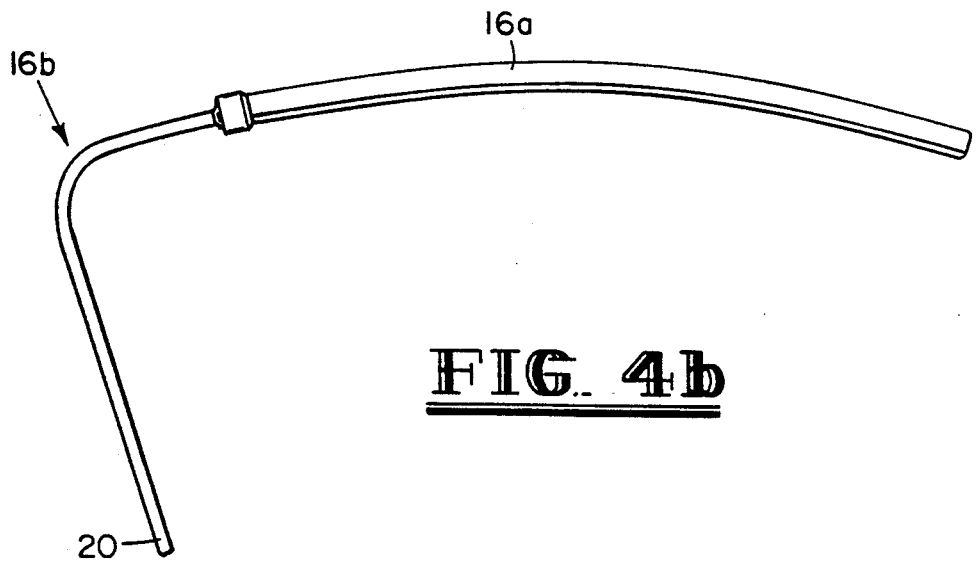
FIG. 4b is a partial elevational view of the rib shaft/rib shaft carriage attachment of Applicant's invention.

Referring again to FIGS. 2a, 2b, 2c, and also to FIGS. 4a and 4b, the rib shaft (16a) is of solid construction and has a lengthwise oriented ridge (not visible in the drawings). The ridge is designed to mechanically interface with the channel (22) when the rib shaft (16a) is telescopically received within interior lumen (24) of the rib sleeve (18) as it is designed to do. While the presence of the channel does tend to weaken the rib sleeve (18) in resisting axial rotation relative to the rib shaft (16a), or vice versa, when a torque is applied to either, the restraining action of the ridge's interface with the channel (22) compensates completely for any such tendency. Prior to incorporating the ridge into the rib shaft (16a) design, experimentation revealed a marked tendency toward such rotation particularly when the prosthetic rib (10) was extended to near its maximum extent.

The rib shaft (16a) and the rib sleeve (18) are formed whereby they jointly define a single arc having a constant radius of curvature regardless of the degree the rib shaft (16a) is received within the rib sleeve (18). The rib sleeve's (18) and rib shaft's (16a) radius of curvature may be adjusted in the manufacturing process according to the expressed preference of the responsible surgeon, as dictated by the physiology of the intended recipient.

Referring principally to FIGS. 2a, 2b, 2c, 3a, 3b, 3c, 4a and 4b, the effective length of the prosthetic rib (10) is determined by the length of the rib sleeve (18) and the degree to which the rib shaft (16a) is telescopically received within the rib sleeve (18). To secure the relative positions of the rib shaft (16a) and the rib sleeve (18) once a desired length is attained, the rib shaft (16a) has a plurality of evenly spaced holes (26) passing therethrough. The rib sleeve (18) of one embodiment has two holes (28) spaced complementarily to the holes (26) in the rib shaft (16a). The holes (28) in the rib sleeve (18) are situated on the outer face of the rib sleeve (18). The rib sleeve carriage attachment (14) also has one hole (30) passing through its sleeve engaging projection (14a).

The holes (26), (28), and (30) are oriented whereby a linear object may concurrently extend through one of the two holes (28) in the rib sleeve (18) and one of holes (26) in the rib shaft (16a) when the rib shaft (16a) is telescopically received within one end of the rib sleeve (18). Likewise, a second linear object may extend through the other hole (28) in the rib sleeve (18) and through hole (30) in the rib sleeve carriage attachment (14) when the sleeve projection (14a) is telescopically received and properly positioned within the other end of the rib sleeve (18).

Referring principally to FIGS. 5a, 5b, 5c and 5d, once the rib shaft (16a) and the rib sleeve (18) are properly, relatively positioned, they are secured using a distraction lock (32). One embodiment of the distraction lock (32) includes a pin (34) long enough to extend through either holes (28) and (26) or through holes (28) and (30) when in position on the assembled prosthetic rib (10), but not long enough to extend beyond the termini of the gripper flanges (36). The tip of the pin (34) as well as the termini of the gripper flanges (36) are rounded. The limit on the length of the pin (34) and the just-referenced rounding are in satisfaction of safety concerns. Sharp edges and slender protrusions are to be avoided in anticipation of the distraction lock (32) possibly becoming dislodged after implantation and have been so avoided in Applicant's preferred embodiment of the distraction lock.

Figure 17:
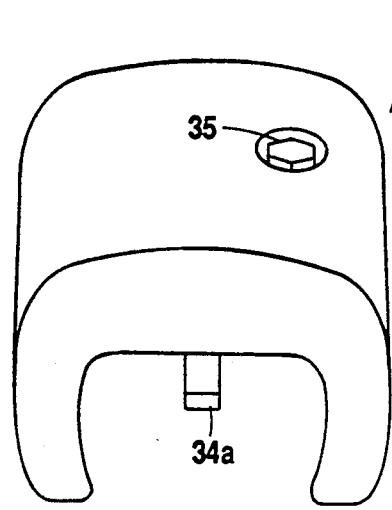
FIG. 17 is a perspective depiction of an alternative embodiment of a distraction lock for use with Applicant's device.
Figure 18:
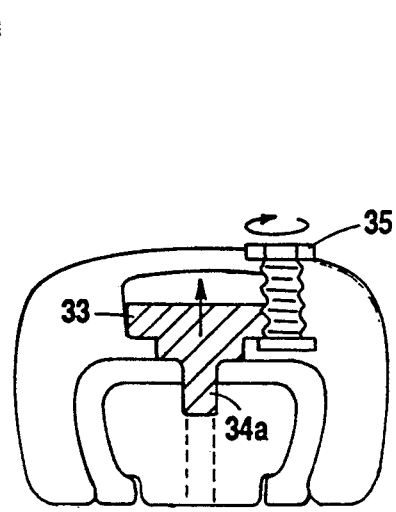
FIG. 18 is an elevational cross section of the distraction lock of FIG. 17.

Referring to FIGS. 17 and 18, an alternative and more desireable embodiment for a distraction lock to be used at the rib shaft end of the rib sleeve (18) is shown (identified generally by the numeral (32a)). In this latter embodiment of the distraction lock (32a), the pin (34a) is incorporated into a plunger-like member (33). The plunger (33) has a head section which is threaded on part of its margin as shown in FIG. 18. A longitudinally immobile hex nut (35) is situated in operative proximity to the plunger (33) and has threads complimentary to those on the plunger (33). Rotation of the hex nut (35) in a first direction withdraws the pin (34a) from holes (26) and (28) respectively of the rib sleeve (18) and the rib shaft (16a) and thereby releases the rib shaft (16a) relative to the rib sleeve (18) to allow the rib (10) to be lengthened (or shortened if appropriate). Rotation of the hex nut (35) in the other direction again extends the pin through holes (26) and (28) and re-stabilizes the rib shaft (16a) relative to the rib sleeve (18). This embodiment of the distraction lock (32a) is preferable for use on the rib shaft end of the rib sleeve (18) because the distraction lock at that end is the one which must be disengaged in order to elongate the prosthetic rib (10), and this embodiment is much easier to disengage than the previously discussed embodiment.

Referring principally to FIGS. 3a and 3b the rib sleeve (18) has two pairs of recesses (29) with which the distraction locks (32) and (32a) are designed to mate. Each recess (29) is formed having a first zone with a depth such that the gripper flanges (36) or (36a) of a distraction lock (32) or (32a) must yield slightly to pass thereover, this zone being nearer the top of the rib sleeve (18). A second zone (31), slightly deeper into the rib sleeve (18), is separated by a palpable line of demarcation visible in FIG. 3b and lies closer to the bottom of the rib sleeve (18). The gripper flanges (36) or (36a) "snap" into the lower, deeper portion of their respective recesses (29) when a distraction lock (32) or (32a) is installed. In this manner, the distraction lock (32) or (32a) is securely held in place until or unless pried from the rib sleeve (18).

An alternative embodiment of the rib sleeve (18) (not shown in the drawings) incorporates multiple pairs of recesses (29) and associated holes (28) near one end of the rib sleeve (18). Such a rib sleeve (18) may be shortened using a hack saw at the time of surgery to shorten the starting, most retracted over-all length for the prosthetic rib (10) leaving a fully functional rib sleeve end having the necessary pair of recesses (29) and hole (28). When shortening this embodiment of the rib sleeve (18), the rib sleeve (18) is simply cut at a point between adjacent pairs of recesses (29) and the cut end is then smoothed using a file. Such an alternative embodiment of the rib sleeve (18) permits its use in situations which otherwise would require the manufacture of a shorter rib sleeve (18). Wider applicability for any one component of Applicant's invention has obvious financial benefits to recipient patients.

The holes (26) in rib shaft (16a) in the preferred embodiment for use in very young children have been spaced in 10 mm intervals in anticipation of the likely growth intervals which will indicate an adjustment of the prosthetic rib (10). Such spacing is in recognition of the fact that only slight misalignment of the spinal column can result in discomfort and possible spinal cord injury.

Referring principally to FIGS. 2a, 2b, 2c, 4a 4b, 6a and 6b, both the rib sleeve carriage attachment (14) and the rib shaft carriage attachment (16b) include two rods (20) at their respective ends. The rods (20) are round in cross section. The rods (20) have a cross sectional diameter of 2 mm in the preferred embodiment.

The rods' (20) round cross sectional shape was chosen as a means for minimizing the biological trauma to the periosteum of the ribs (12) and to the inferior surfaces of the ribs (12) where the rods (20) have their primary contact therewith (to be discussed in more detail hereinafter).

The specific 2 mm diameter of the rods (20) was chosen after numerous alternative specifications were tested. A 2 mm diameter of CP Titanium has proven to provide the optimum balance between the flexibility necessary for safe manipulation during implantation and strength necessary for post-implantation stability. No other material tested in a 2 mm rod configuration and no other dimension in CP Titanium provided the preferred characteristics for the rods (20).

The rods (20) of the preferred embodiment are 76 mm in length. This length has been shown through experimentation to provide a quite acceptable degree of surplus length to facilitate the needed manipulation during implantation both to circumvent the natural ribs (12) at the basic level, as well as to adjust the orientation and position of the loops formed from the rods (20) in determining the over-all orientation of the prosthetic rib (10) within the patient. The indicated length does not, however, introduce excessive length which would impede maneuvering during implantation and require excessive bending to avoid surrounding tissues.

Referring principally to FIGS. 1, 7a, 7b, 7c and 7d, the rods (20) are during the implantation procedure manipulated by the surgeon to circumvent the appropriate natural rib (12). The path of the rods (20) about the natural rib (12) is essentially circular when properly implanted, even though the rib would be better described as oblong. This is an important aspect of practicing Applicant's invention for several independently significant reasons. The circular circumvention permits the carriage attachments (14) and (16b) to pivot relative to the natural ribs (12). This is important, in part, because the carriage attachments (14) and (16b) change orientation relative to the ribs (12) to which they are attached as the length of the prosthetic rib (10) is changed subsequent to implantation.

Referring principally to FIGS. 8a and 8b, the ability of the carriage attachments (14) and (16b) to pivot is further important in allowing the prosthetic rib (10) to partially accommodate traumatic force which may occur in falls, etc. while not transferring the force to the natural ribs (12) in a manner which would likely fracture the natural ribs (12). If the carriage attachments (14) and (16b) were rigidly attached to natural ribs (12), the carriage attachments (14) and (16b) would apply a possibly damaging torque to the natural ribs (12) in response to a traumatic force to the rib shaft (16a) and/or rib sleeve (18). This is substantially avoided by the circular path of circumvention suggested herein. Also, the relatively loose circumvention of the natural ribs (12) obviates the danger of rib ischemia at the site of contact between the rods (20) and the natural rib (12) surface. Still further, the gentle movement permitted by the preferred mode of attachment for the prosthetic rib (10) and brought about by normal movement of the recipient has the tendency to promote work hypertrophy thereby actually strengthening the natural rib (12).

When the prosthetic rib (10) is properly implanted and adjusted, the rods' (20) principal contact with the natural ribs (12) are to inner surface areas of the natural ribs (12) relative to the intervening chest wall defect. In this manner, the rods (20) "cradle" the natural ribs (12) at a point of minimum contact as opposed to deleteriously compressing them.

Figure 9A:
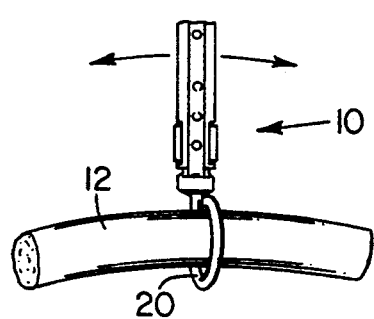
FIG. 9a is a perspective representation of a means of attachment not taught by Applicant shown to demonstrate the comparative stability of Applicant's preferred embodiment.
Figure 9B:
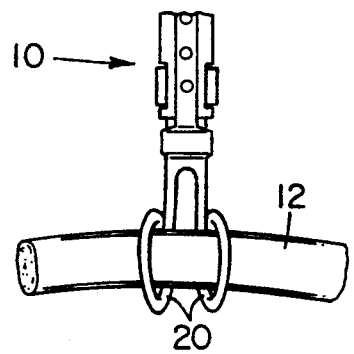
FIG. 9b is a partial perspective representation of one of Applicant's carriage attachments depicting the stability provided by the dual rods included therein.
Figure 10:
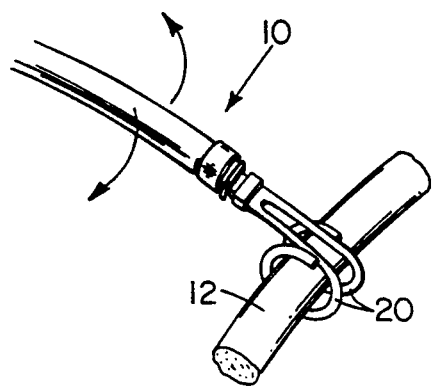
FIG. 10 is a partial perspective representation of one of Applicant's carriage attachments depicting the stability provided by the dual rods included therein.

Referring principally to FIGS. 9a, 9b and 10, the rods (20) number two for each of the carriage attachments (14) and (16b) in satisfaction of some of Applicant's material objectives in designing the preferred embodiment. Most notably, dual attachment sites for the carriage attachments (14) and (16b), as opposed to a singular attachment site, provide substantial rotational stability for the prosthetic rib (10). As illustrated by FIGS. 9a and 9b, a single site of attachment will do little to stabilize the prosthetic rib (10) against even minor deflective forces while a dual attachment quite ably resists such force. Also, the cumulative mass of titanium needed for strength of the attachment to the natural ribs (12) can be divided between the two rods (20) as opposed to being embodied in a single, larger rod. Such a single rod would be too stiff to safely manipulate during implantation if it incorporated the same quantum of titanium as is divided between the two rods (20) of each carriage attachment (14) and (16b) of the preferred embodiment.

It is noted that the use of three or more rods (20) is not recommended because of the associated consumption of surface space on the natural ribs (12) and the minimal additional stability which would be achieved. Because a plurality of prosthetic ribs (10) will be required in most situations requiring any use of the prosthetic rib (10), conservation of natural rib (12) surface space is desired.

Figure 11A:
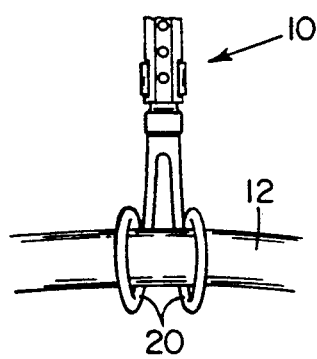
FIGS. 11a and 11b are elevational representation of one of Applicant's carriage attachments with the rods thereof affixed to the natural rib whereby the prosthetic rib projects perpendicularly from the rib surface.
Figure 11B:
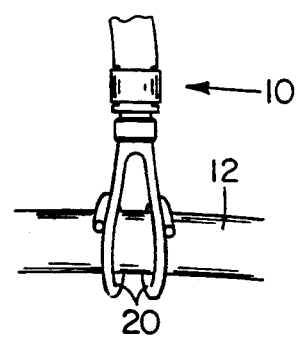
Figure 11C:
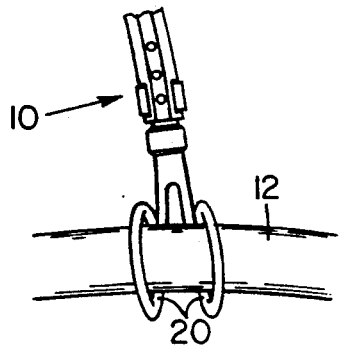
FIGS. 11c and 11d are elevational representations of one of Applicant's carriage attachments with the rods thereof affixed to the natural rib whereby the prosthetic rib projects obliquely from the rib surface.
Figure 11D:
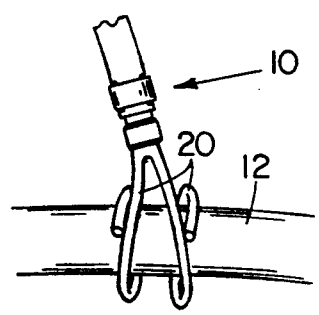
Figure 12:
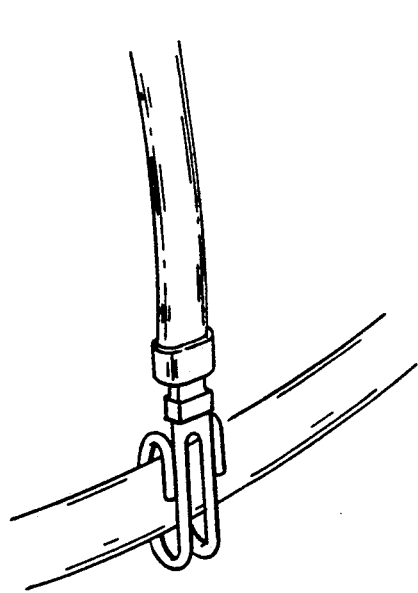
FIG. 12 is a representation of one of Applicant's carriage attachments with the rods thereof affixed to the natural rib is aligned with the vertical axis of the recipient's body notwithstanding the transverse projection of the natural rib.

Referring principally to FIGS. 11a, 11b, 11c, 11d, and 12, a perhaps less apparent benefit of dual rods (20) with a certain degree of surplus length lies in the flexibility provided to the surgeon in orienting the prosthetic rib (10) relative to the natural ribs (12) to which the prosthetic rib (10) is attached. As shown in FIG. 12, the portions of the ribs (12) to which a prosthetic rib (10) is attached are seldom precisely perpendicular to the desired lengthwise orientation of the prosthetic rib (10). By looping the rods (20) at different positions along their length, the over-all prosthetic rib (10) can be oriented in any desired manner. Particularly where the variance from a perpendicular orientation is notably pronounced, the duel rods (20) cooperate to minimize the chance of slippage along the natural rib (12).

Referring principally to FIGS. 11c and 11d, the surgeon may not want the prosthetic rib (10) to be oriented with the convexity of the rib shaft (16a) and the rib sleeve (18) extending "radially" from the patient. The dual rods (20) permit appropriate three dimensional alignment of the prosthetic rib (10) without sacrificing stability of its attachment to the natural ribs (12). The loops formed from the rods (20) may be situated in an eccentric relationship whereby the respective carriage attachment (14) or (16b) is directed obliquely relative to the path of the natural rib (12).

Figure 13:
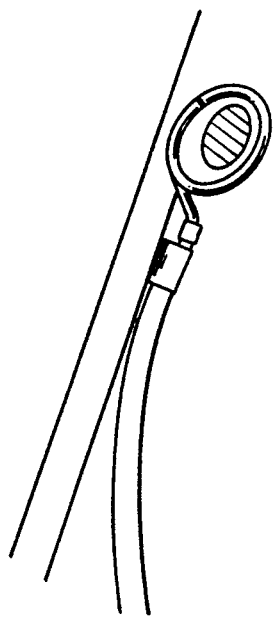
FIG. 13 is a representation of the manipulation of the rods of Applicant's carriage attachments which permits inward adjustment of the over-all prosthetic rib.

Referring principally to FIG. 13, there are occasions when anatomical consideration require that the maximum radial extension of the prosthetic rib (10) be reduced and that the respective origination and termination of the combined rib shaft (16a) and rib sleeve (18) are accordingly adjusted medially relative to the outermost surfaces of the relevant natural ribs (12). The above-referenced surplus length of the rods (20) is further instrumental in permitting any such necessary adjustment as can be seen from the drawing.

The surgical procedure involved in implantation of the prosthetic rib is outlined as follows:

The patient is placed in a lateral decubitus position. The arm on the side of the procedure is free draped to allow for positioning during surgery. A longitudinal, curvi-linear incision is then made over the area of the chest wall defect and carried down to the level of the defect. The skin flaps are then developed proximal and distal and are retracted. The natural, vestigial ribs that are present proximal and distal to the chest wall defect are isolated. The prosthesis site is first selected posteriorly. The fully assembled prosthetic rib is then vertically positioned in the most posterior position of the chest wall defect, and the two rods extending from each carriage attachment are placed overlying the natural ribs and the sites are marked with a cutting cautery. The prosthetic rib is then removed and a clamp is used to pierce the intercostal muscle overlying the natural rib at each site with the lung safely held away from the clamp. Thus, two holes are placed over the superior surface of the natural rib where the prosthetic rib will be placed. A similar procedure is repeated at the area immediately inferior to the natural, vestigial rib at inferior limit of the chest wall defect.

The prosthetic rib is replaced over the chest wall defect and the two rods of each carriage attachment are bent toward the chest wall cavity at a near right angle to the length of the assembled rib shaft and rib sleeve. The rods of the rib shaft carriage attachment are inserted partway through the incisions over the superior surface of the superior natural rib. The rods of the rib sleeve carriage attachment are inserted partway through the incisions under the inferior surface of the inferior natural rib.

Next, the lung is again retracted, the rib sleeve is disengaged from the rib shaft and from the rib sleeve carriage attachment so that both carriage attachments can be rotated so that the respective rods inside the chest cavity are brought out toward the surgeon for visualization in the chest wall defect. The rib shaft carriage attachments are sequentially held in place as the surgeon, using pliers or a suitable substitute, manipulates the rods to circumvent the natural ribs in a circular, minimally pitched spiral configuration with the most distal portion of each rod coming to closely juxtapose its proximal origin exterior to the chest cavity (See FIG. 15b). The only interthoracic portions of the carriage attachments are the curved, smooth surfaces of the rods.

Once the rods are configured about the natural ribs, the rib sleeve is re-engaged with the rib shaft and the engaging projection of the rib sleeve carriage attachment to allow final positioning of the prosthetic rib assembly. The radius & length of the rods are adjusted to provide final position of the actual over all prosthetic rib assembly. By appropriately bending and orienting the rods over-all position of the prosthetic rib assembly may be brought further into the chest wall defect to allow for clearance of neurovascular bundles of the arm. Also the loops formed of the rods can be adjusted to lie eccentrically to orient the rib shaft and rib sleeve in an anterior lateral or posterior lateral position.

Once final positioning of the first prosthetic rib assembly is attained, a suitable plurality of prosthetic ribs are implanted as just described in an anterior progression until the chest wall defect is adequately overlain.

Figure 15A:
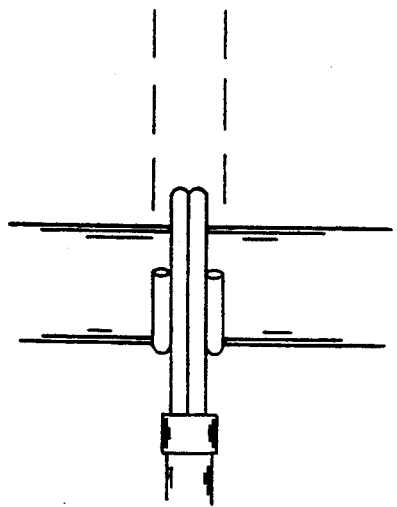
FIG. 15a is a representation of rods improperly spaced on a recipient natural rib.
Figure 15B:
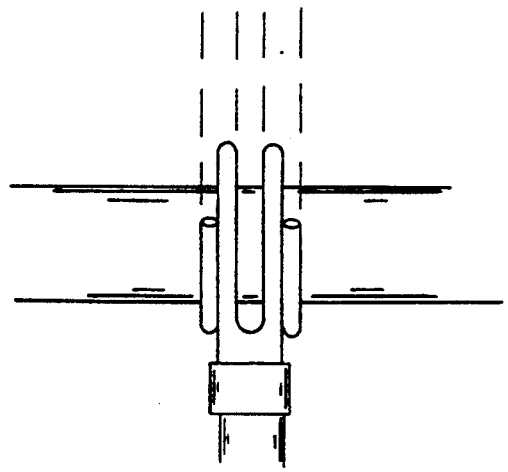
FIG. 15b is a representation of rods properly spaced on a recipient natural rib.

In the implantation procedure, care is taken that the two rods of each carriage attachment are separated by an adequate distance to allow for blood supply of the natural rib between them (See FIGS. 15a and 15b). Once the desired number of prosthetic ribs are satisfactorily in position, distraction locks installed as previously described herein.

Figure 16A:
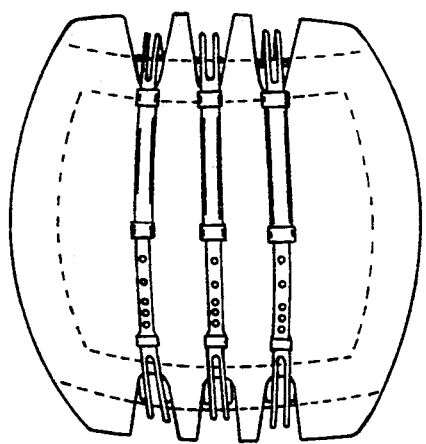
FIG. 16a is a representation of an implanted sheet of medical elastomeric plastic material underlying Applicant's prosthetic ribs.
Figure 16B:
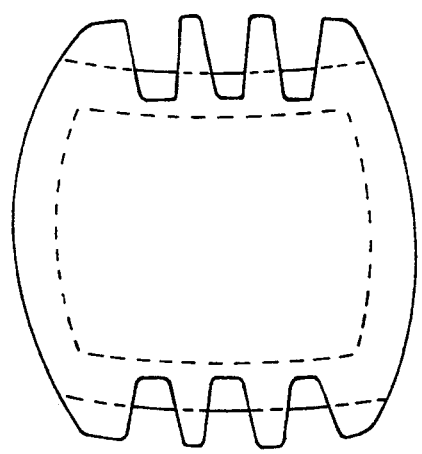

Referring to FIGS. 16a and 16b, a dacron, reinforced, Silastic sheet of at least 0.030 inch thickness is, in some cases, next measured to cover the chest wall defect and overlap it to a distance of approximately 2 centimeters in all dimensions. Slots are cut in the material where the carriages are piercing the chest wall and the center portion and the narrow strip of material should be threaded between the carriage shafts for each prosthesis. The silastic sheet is then placed underneath the prosthesis and provides an interface between the lung surface and the metal of the prosthesis. The periphery of the silastic sheet is sutured in each corner and, utilizing a zero proline suture, the plastic sheet is attached at two inch intervals along each prosthetic rib to tether it up to the external chest wall formed by the prosthetic ribs. If natural pleura is present, it is sewn directly to the underside of the prosthetic rib (10) with Proline suture. If desirable a Goretex sheet cab be introduced between the lung and prosthetic rib (10) without the need for subsequent removal. Chest tubes are then inserted inside the thoracic cavity to fully expand the lungs and then the skin surface is closed in the usual surgical manner.

Figure 19:
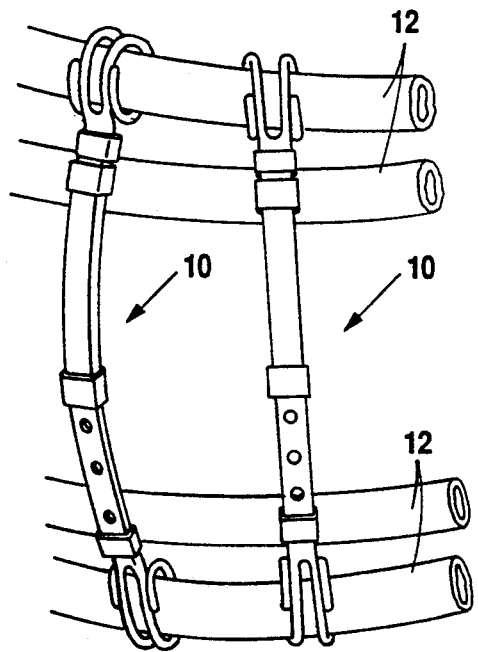
FIG. 19 is a perspective view of two prosthetic ribs attached to natural ribs other than those immediately adjacent to a chest wall defect.
Figure 20:
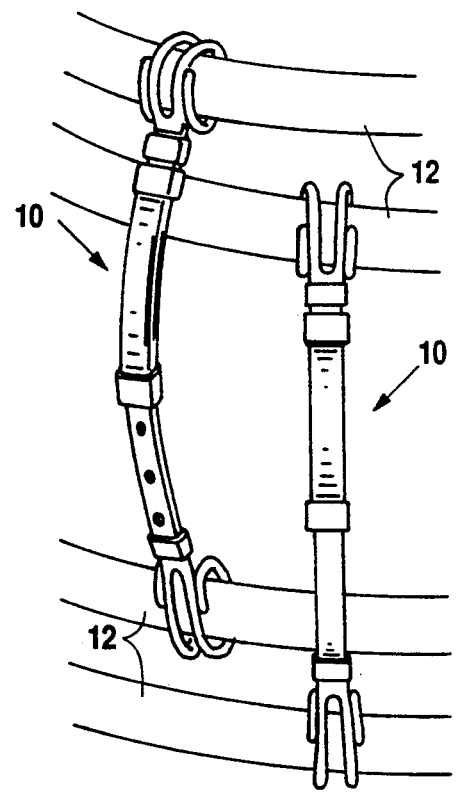
FIG. 20 is a perspective view of a staggered arrangement for multiple prosthetic ribs attached to natural ribs other than those immediately adjacent to a chest wall defect.

Referring to FIGS. 19 and 20, it should not be inferred from the above-described surgical procedure that attachment of the prosthetic rib(s) (10) to natural ribs (12) immediately adjacent to the chest wall defect is the only appropriate procedure. Attachment to natural ribs (12) more distant from the defect may be desireable in some cases. The curvature of the prosthetic rib (10) is such that it should substantially conform to any segment of the chest wall and overlying existing natural ribs (12) will generally not pose serious problems.

The possible benefits from attachment to ribs other than those immediately adjacent to chest wall defects include allowing for more growth in the recipient than a smaller prosthetic rib (10) can accommodate. By having a prosthetic rib (10) long enough to span beyond the natural ribs (12) at the margin of the chest wall defect, substantial later grown can be accommodated by changing the points of attachment to natural ribs (12) at or closer to the margin of the chest wall defect. In this manner, complete change out of the prosthetic rib (10) may be avoided, or at least delayed substantially. Referring particularly to FIG. 20, attachment to staggered natural ribs (12) may be a means for distributing load on natural ribs (12) in the event of an impact to the involved chest region. Still further, this arrangement permits a surgeon to avoid an unacceptable attachment site on one of the natural ribs immediately adjacent to the chest wall defect.

As a still further alternative arrangement for implantation, each rod (20) on either end of the prosthetic rib (10) may be attached to different ribs (not shown in any drawings). In such a case, one prosthetic rib (10) would be attached to four natural ribs (12). This may be particularly desireable when the available natural ribs are, for whatever reason, not adequately strong or rigid.

Figure 14A:
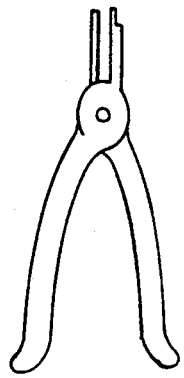
FIG. 14a is a representation of the pliers used to adjust the length of an implanted prosthetic rib.
Figure 14B:
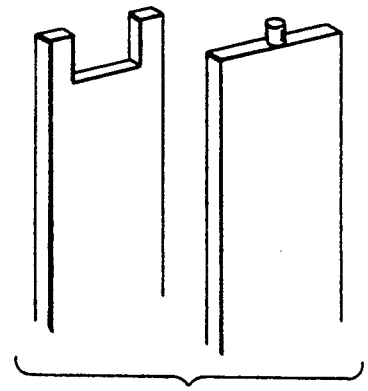
Figure 14C:
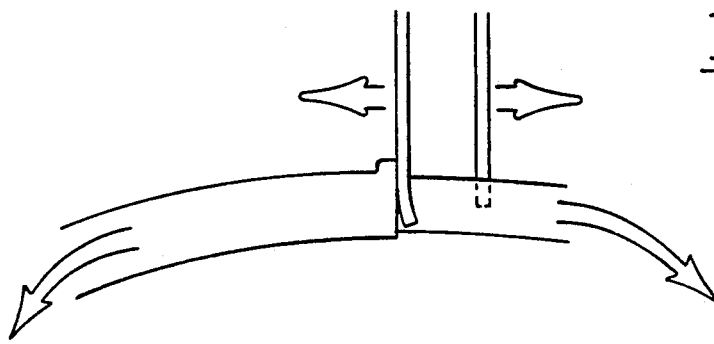
FIG. 14c is a representation of the pliers of FIG. 14a in position to adjust the rib shaft relative to the rib sleeve.

The surgical procedure involved in adjusting the length of the previously implanted prosthetic rib is outlined as follows:

The patient under general anaesthetic has an incision made in the scar from the original implantation. Once this is done the skin flap is minimally dissected down toward the distraction locks securing the rib shaft relative to the rib sleeve. Once distraction locks are located, they are removed from each of the prosthetic ribs except the central most one (if the alternative embodiment of the distraction lock (32a) as described herein is used, the hex nut (35) will be adjusted to disengage the pin (34a) and the distraction lock (32a) need not be removed). Next, distraction pliers (shown in FIGS. 14a, 14b, and 14c) are engaged with the central most prosthetic rib and the last distraction lock is removed. The distraction pliers are used to lengthen the central most prosthetic rib to the desired extent to expand the affected chest cavity to the length of the normal chest cavity. Once this adjustment is performed, distraction locks are placed on all prosthetic ribs to secure their adjusted lengths and states. The silastic sheet's edges are drawn further to the edges of the actual borders of the chest wall defect and the proline suture which is tethering the silastic sheet to the undersurface of the ribs slides on top of the body of the prosthetic ribs. Once this is accomplished, a radiograph checks their final position and the skin gets closed in the usual fashion. No chest tubes are needed.

B. Use of Applicant's Invention in the Treatment of Scoliosis

The preceding discussion centered on use of Applicant's prosthetic rib (10) as an effective replacement for natural ribs which are actually or effectively absent. An alternative use of Applicant's device is in the treatment of scoliosis.

Figure 21:
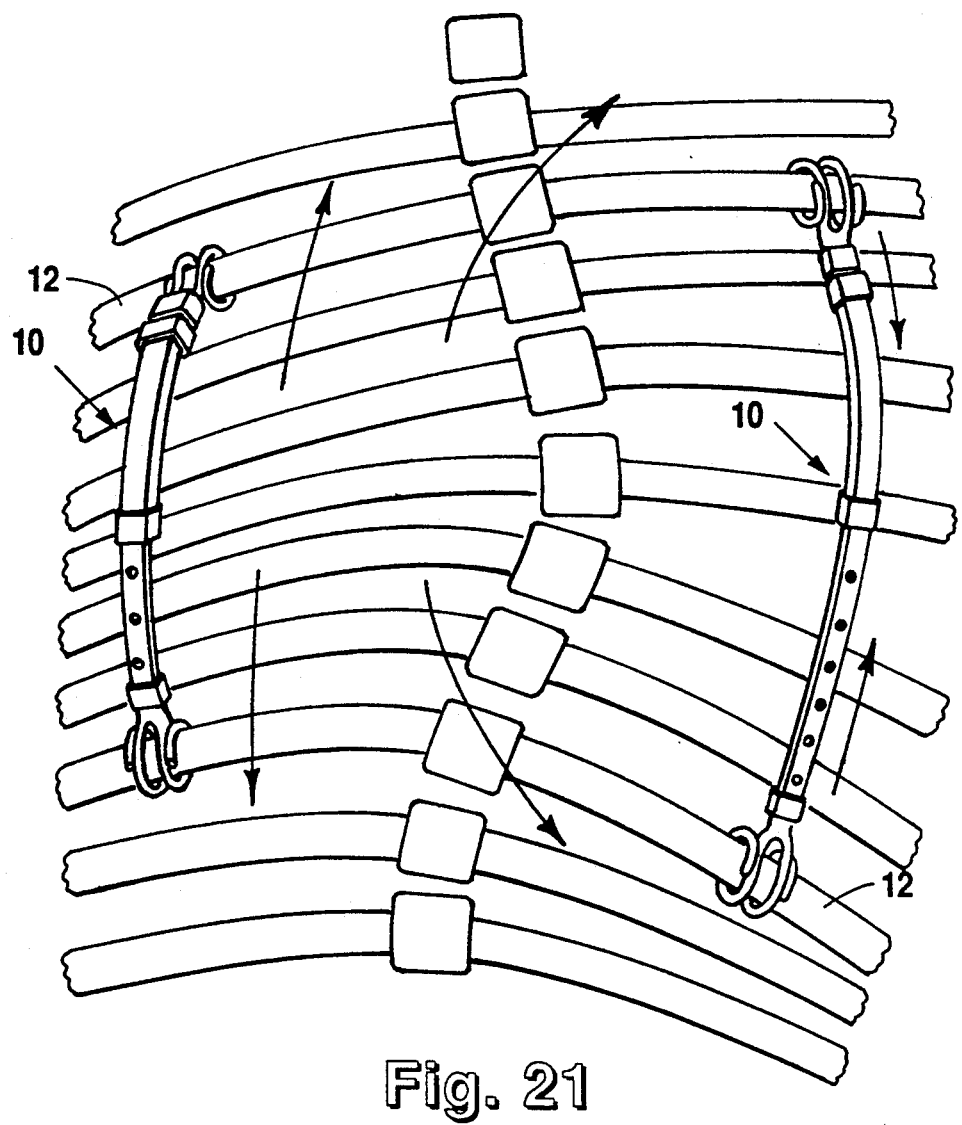
FIG. 21 is a perspective view of Applicant's prosthetic rib used in the treatment of scoliosis.

Referring to FIG. 21, the vertebral column of a scoliosis sufferer develops at least one lateral curvature which, when viewed posteriorly or anteriorly, exhibits clearly evident convex and concave sides.

Using the prosthetic rib (10) in treating scoliosis involves attaching the rib (10) to natural ribs (12) respectively near the superior and inferior limits of the deformity and on the concave side thereof. The optimum over-all length of the prosthetic rib (10) for this application should be such that the rib (10) applies an expansive force which separates the natural ribs (12) such that the vertebral column is necessarily straightened (at least to some degree). This optimum length may be maintained notwithstanding subsequent growth of the recipient by virtue of the previously discussed adjustability of the prosthetic rib (10).

Referring again to FIG. 21, one or more additional prosthetic ribs (10) may be used on the convex side of a scoliosis deformity, fully extended and thereafter sequentially shortened to apply a compressive force to ribs on the convex side of the deformity and thereby to compliment the corrective action of the rib (10) on the concave side.

C. Use of Applicant's Device in the Immobilization of Fractured Ribs and in Cosmetic Surgery Applications Ribs which are fractured through accidental trauma or the treatment of aesthetically undesirable rib deformities such as are exhibited in the form of rib humps or chest concavities must be immobilized in the desired orientation during the bone mending process.

Figure 22:
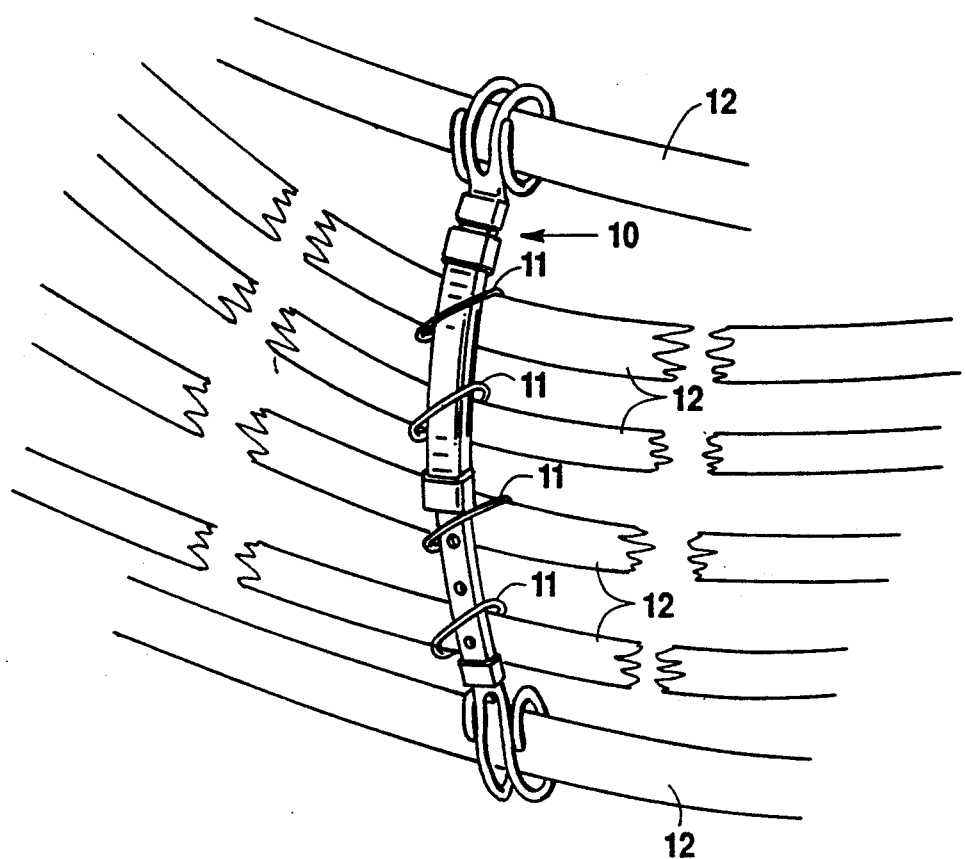
FIG. 22 a perspective depiction of fractured natural ribs immobilized by Applicant's prosthetic rib.

Referring to FIG. 22, fractured natural ribs (12) may be anchored to Applicant's prosthetic rib (10) to immobilize the natural ribs (12) during the mending process. A sling (11) may be constructed of titanium wire to secure the natural rib(s) to the prosthetic rib (10).

Figure 23:
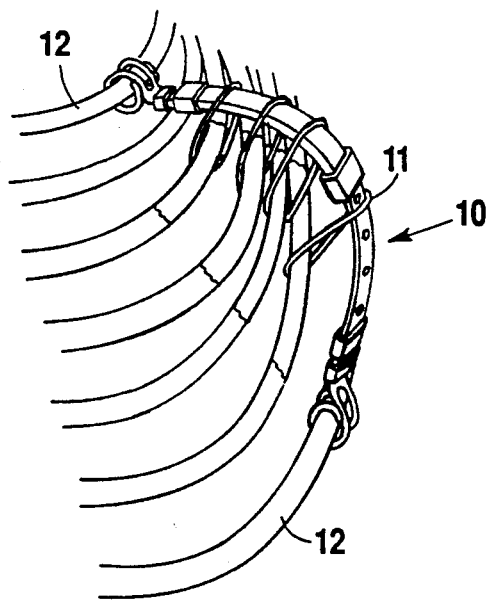
FIG. 23 is a perspective depiction of Applicant's prosthetic rib used in the correction of a rib deformity prior to elongation of the involved natural ribs.
Figure 24:
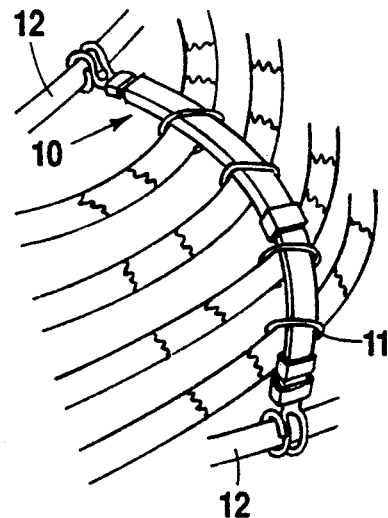
FIG. 24 is a perspective depiction of Applicant's prosthetic rib used in the correction of a rib deformity after elongation of the involved natural ribs.
Figure 25:
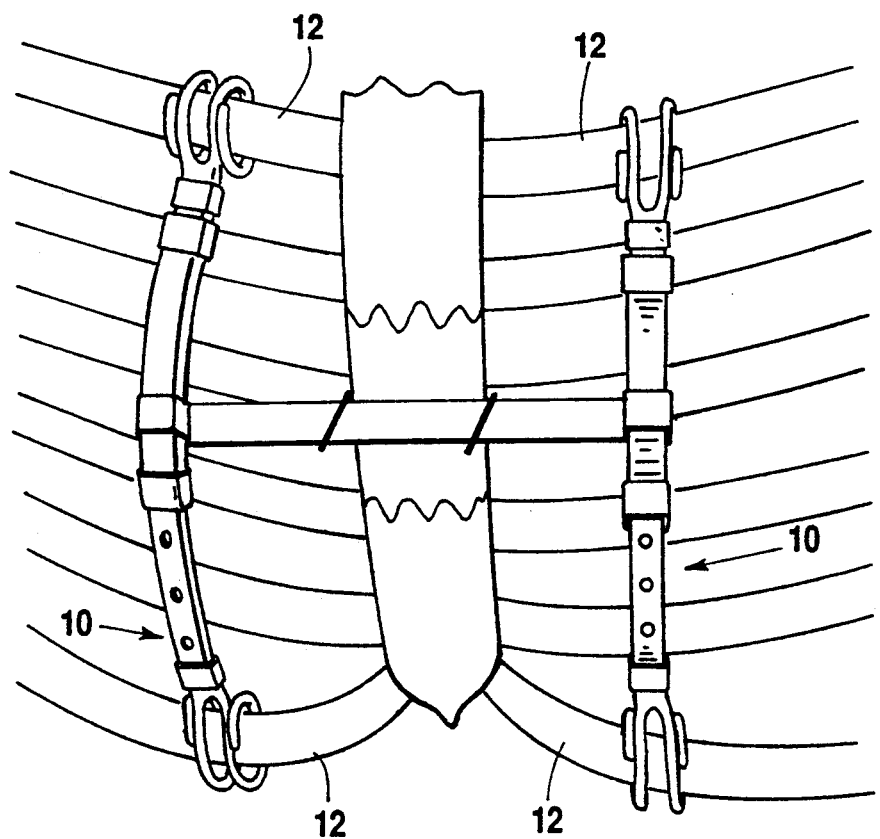
FIG. 25 is a perspective view of a pair of Applicant's prosthetic ribs situated on either side of the sternum of a patient and a cross bar spanning therebetween, such structure used in the correction of an anterior chest concavity.

Referring to FIGS. 23 and 24, a chest concavity may be treated by elongating as well as re-orienting the natural ribs (12). The prosthetic rib (10) is well suited for involvement in such treatment because of its capacity to be extended. As the involved natural ribs (12) are appropriately prepared for elongation, the prosthetic rib (10) to which the natural ribs (12) are attached is extended thereby applying the elongating, outwardly directed force.

It is noted that this same procedure may be used by plastic surgeons to address benign, yet aesthetically objectionable chest contours. Expanding the rib structure at appropriate locations could, for example, be used to appropriately enlarge the male or female upper chest to achieve cosmetic objectives.

Figure 26A:
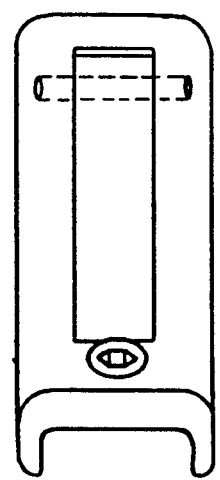
FIGS. 26a, 26b and 26c are top, side and side cross section views of an alternative embodiment of the rib sleeve of Applicant's invention which incorporates a locking mechanism as a substitute for the distraction locks describe elsewhere in the application.
Figure 26B:
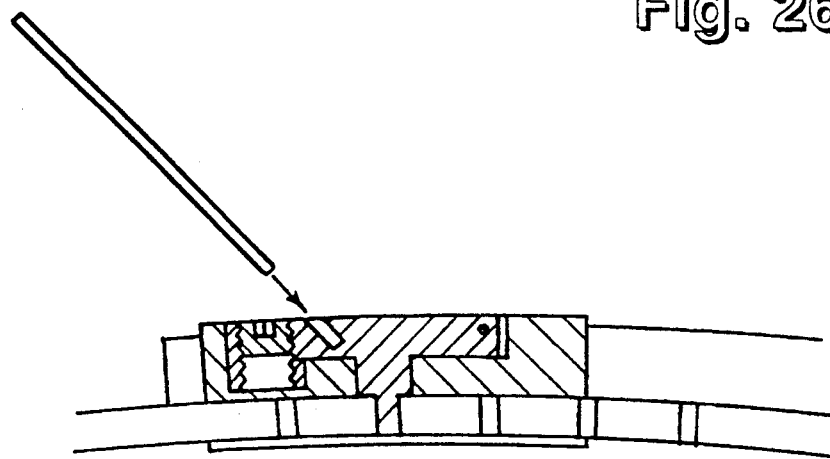
Figure 26C:
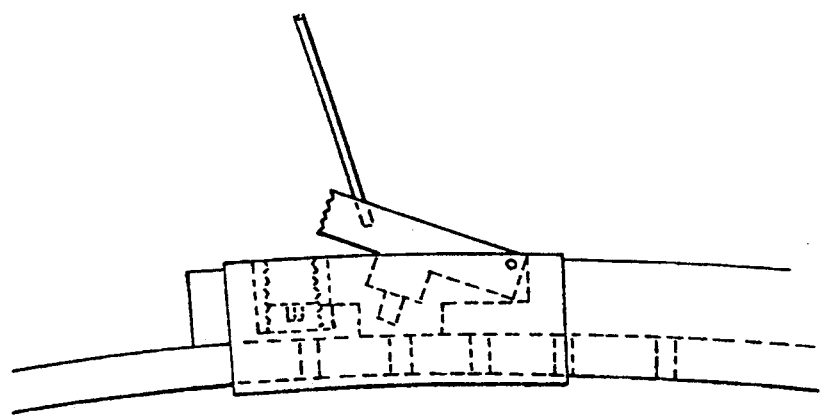

Referring to FIG. 26, yet another alternative embodiment of the rib sleeve (18) is shown. This alternative embodiment includes a trap door-like member which incorporates a pin which, in turn, corresponds to the pin (34) or (34a) of the distraction locks (32) or (32a) previously discussed. This embodiment of the rib sleeve (18) will obviate the need for a separate distraction lock (32) or (32a).

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A method of treating curvature of the vertebral column associated with scoliosis comprising the steps of:

surgically accessing a first natural rib of a recipient near one margin of a vertebral column deformity on the concave side of said deformity and attaching a first end of a prosthetic rib to said first natural rib, said prosthetic rib comprising:
  a prosthetic rib shaft having a lateral prosthetic rib shaft end and a medial prosthetic rib shaft end, prosthetic rib shaft stabilizing means being formed at said lateral prosthetic rib shaft end for securing said prosthetic rib shaft to a skeletal component of a recipient of said prosthetic rib;
  a prosthetic rib sleeve, said prosthetic rib sleeve having a lateral prosthetic rib sleeve end, a medial prosthetic rib sleeve end, and a channel passing continuously through said prosthetic rib sleeve and opening at both said rib sleeve ends, said channel having dimensions whereby said medial end of said prosthetic rib shaft may be telescopically received therein;
  prosthetic rib sleeve stabilizing means for securing said prosthetic rib sleeve to a skeletal component of a recipient of said prosthetic rib, said prosthetic rib sleeve stabilizing means having a sleeve stabilizing means projecting with dimensions whereby said projection sleeve stabilizing means may be telescopically received within said channel at said lateral prosthetic rib sleeve end;
surgically accessing a second natural rib of said recipient near the other margin of said vertebral column on said concave side of said deformity and attaching a second end of said prosthetic rib to said second natural rib;
adjusting said prosthetic rib whereby it applies an expansive force to said first and second natural ribs thereby tending to move said first and second natural ribs relative to each other whereby the curvature of the portion of said vertebral column between and including the vertebrae of which said first and second natural ribs are continuous parts is reduced.

2. The method of claim 1 wherein said prosthetic rib shaft stabilizing means comprise a plurality of rods extending from said lateral prosthetic rib shaft end, said rods being made of a sufficiently malleable material and being of sufficient length whereby said rods may be manipulated to circumvent a natural rib of said recipient and thereby secure said prosthetic rib shaft within said recipient.

3. The method of claim 2 wherein said prosthetic rib sleeve stabilizing means comprise a plurality of rods attached to and extending outwardly from said lateral prosthetic rib sleeve, said rods being made of a sufficiently malleable material and being of sufficient length whereby said rods may be manipulated to circumvent a natural rib of said recipient and thereby secure said prosthetic rib sleeve within said recipient.

4. The method of claim 3 wherein said prosthetic rib sleeve has first and second sleeve locking holes, said first sleeve locking hole being situated near said medial prosthetic rib sleeve end and said second sleeve locking hole being situated near said lateral prosthetic rib sleeve end, said prosthetic rib shaft having a plurality of shaft locking holes spaced along the length of said shaft, passing at least partially therethrough and oriented whereby a first linear pin member may pass simultaneously through said first sleeve locking hole and into one of said shaft locking holes, said prosthetic rib sleeve stabilizing means projection having a projection locking hole passing at least partially therethrough and oriented whereby a second linear pin member may pass simultaneously through said second sleeve locking hole and into said projection locking hole.

5. The method of claim 4 wherein said prosthetic rib further comprises a resilient snap-on lock member comprising a pin member for extending through a first one of said shaft locking holes and said first sleeve locking hole or through said projection locking hole and said second sleeve locking hole, said lock further comprising first and second gripper flanges on either side of said pin, said gripper flanges being shaped whereby interior space defined by said gripper flanges may snugly receive a length of said prosthetic rib sleeve when forced thereon against a slight resilient force applied by said gripper flanges, said pin being situated whereby said pin extends through said first one of said shaft locking holes and said first sleeve locking hole or through said projection locking hole and said second sleeve locking hole when said lock is positioned on said length of said prosthetic rib sleeve, said resilient force maintaining said lock in place on said length of said prosthetic rib sleeve unless forcibly removed therefrom.

6. A method of immobilizing a fractured natural rib comprising the steps of:
 surgically accessing a first unfractured natural rib of a recipient superior to said fractured natural rib and attaching a first end of a prosthetic rib to said first unfractured natural rib, said prosthetic rib comprising:
  a prosthetic rib shaft having a lateral prosthetic rib shaft end and a medial prosthetic rib shaft end, prosthetic rib shaft stabilizing means being formed at said lateral prosthetic rib shaft end for securing said prosthetic rib shaft to a skeletal component of a recipient of said prosthetic rib;
  a prosthetic rib sleeve, said prosthetic rib sleeve having a lateral prosthetic rib sleeve end, a medial prosthetic rib sleeve end, and a channel passing continuously through said prosthetic rib sleeve and opening at both said rib sleeve ends, said channel having dimensions whereby said medial end of said prosthetic rib shaft may be telescopically received therein;
  prosthetic rib sleeve stabilizing means for securing said prosthetic rib sleeve to a skeletal component of a recipient of said prosthetic rib, said prosthetic rib sleeve stabilizing means having a sleeve stabilizing means projection with dimensions whereby said projection sleeve stabilizing means may be telescopically received within said channel at said lateral prosthetic rib sleeve end;
 surgically accessing a second unfractured natural rib of said recipient inferior to said fractured natural rib and attaching a second end of said prosthetic rib to said second unfractured natural rib, said prosthetic rib being oriented whereby a portion thereof overlies a fractured portion of said fractured natural rib;
 harnessing a segment of said fractured natural rib to said prosthetic rib by attachment means; and
 adjusting said prosthetic rib whereby said segment of said fractured natural rib attached to said prosthetic rib is maintained in a desired orientation.

* * * * *